US00PP19616P2

(12) United States Plant Patent
Kawashima et al.

(10) Patent No.: US PP19,616 P2
(45) Date of Patent: Jan. 6, 2009

(54) NEW GUINEA IMPATIENS PLANT NAMED 'SAKIMP010'

(50) Latin Name: *Impatiens×hybrida*
Varietal Denomination: 'SAKIMP010'

(75) Inventors: Moriya Kawashima, Yokohama (JP); Yoneo Kobayashi, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/011,590

(22) Filed: Jan. 28, 2008

(51) Int. Cl.
*A01H 5/00* (2006.01)

(52) U.S. Cl. ..... Plt./318.2

(58) Field of Classification Search ..... Plt./318.2, Plt./318
See application file for complete search history.

*Primary Examiner*—Annette H Para
(74) *Attorney, Agent, or Firm*—Jondle & Associates, P.C.

(57) ABSTRACT

A New Guinea *Impatiens* cultivar particularly distinguished by having white flowers with a very light pink tint, a strong root system and a vigorous and branching growth habit, is disclosed.

1 Drawing Sheet

Genus and species: *Impatiens×hybrida* (hort).
Variety denomination: 'SAKIMP010'.

BACKGROUND OF THE NEW PLANT

The present invention comprises a new and distinct cultivar of New Guinea *impatiens,* botanically known as *Impatiens×hybrida* (hort), and hereinafter referred to by the cultivar name 'SAKIMP010'. 'SAKIMP010' originated from an interspecific hybridization occurring in Misato, Japan between the female parent, 'NG-01WD', an unpatented proprietary *Impatiens* breeding line with white flowers and the male parent, 'EL-1A-2', an unpatented proprietary *Impatiens* breeding line with lilac flowers.

In February 2002, the female parent line, 'NG-01WD', and male parent line, 'EL-1A-2', were crossed and a population of $F_1$ plants was created. The $F_1$ plants were evaluated in Misato, Japan in an open field trial. The criteria for plant selection included flower color, strong root system and a compact plant growth habit. At the completion of the trial, one single-plant selection was made based on the above criteria and vegetatively propagated. From May to August 2005, the selection was evaluated in an open field in Misato, Japan. Shoot-tip cuttings of the variety were then shipped to Salinas, Calif., where the plants were regenerated and reevaluated for stability of traits. The selection subsequently was named 'SAKIMP010' and found to have its unique characteristics reproduce true to type in successive generations of asexual propagation.

SUMMARY OF THE INVENTION

The following are the most outstanding and distinguishing characteristics of this new cultivar when grown under normal horticultural practices in Salinas, Calif.

1. A vigorous and branching growth habit;
2. White flowers with a very light pink tint; and
3. A strong root system.

DESCRIPTION OF THE PHOTOGRAPHS

This new impatiens plant is illustrated by the accompanying photographs which show overall plant habit including blooms, buds, and foliage of the plant; the colors shown are as true as can be reasonably obtained by conventional photographic procedures. The photographs are of plants that are 5 months from their transplanting date and 6 months from the stick date.

DETAILED DESCRIPTION OF THE NEW CULTIVAR

Figure 1:
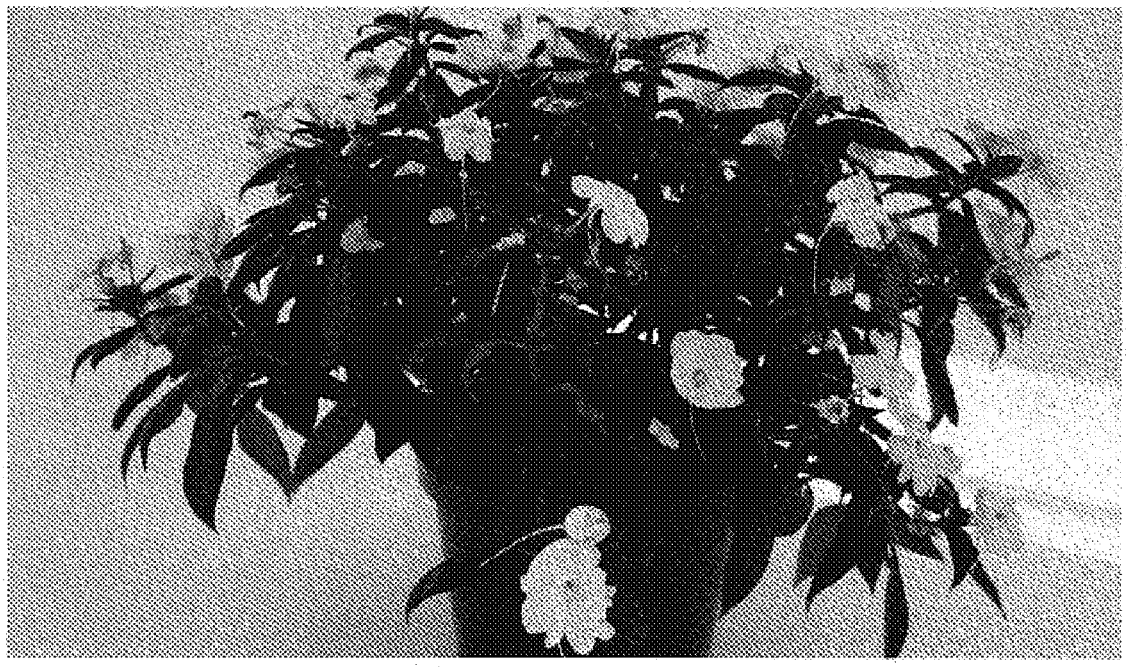
FIG. 1 shows the overall plant habit including blooms, buds and foliage.
Figure 2:
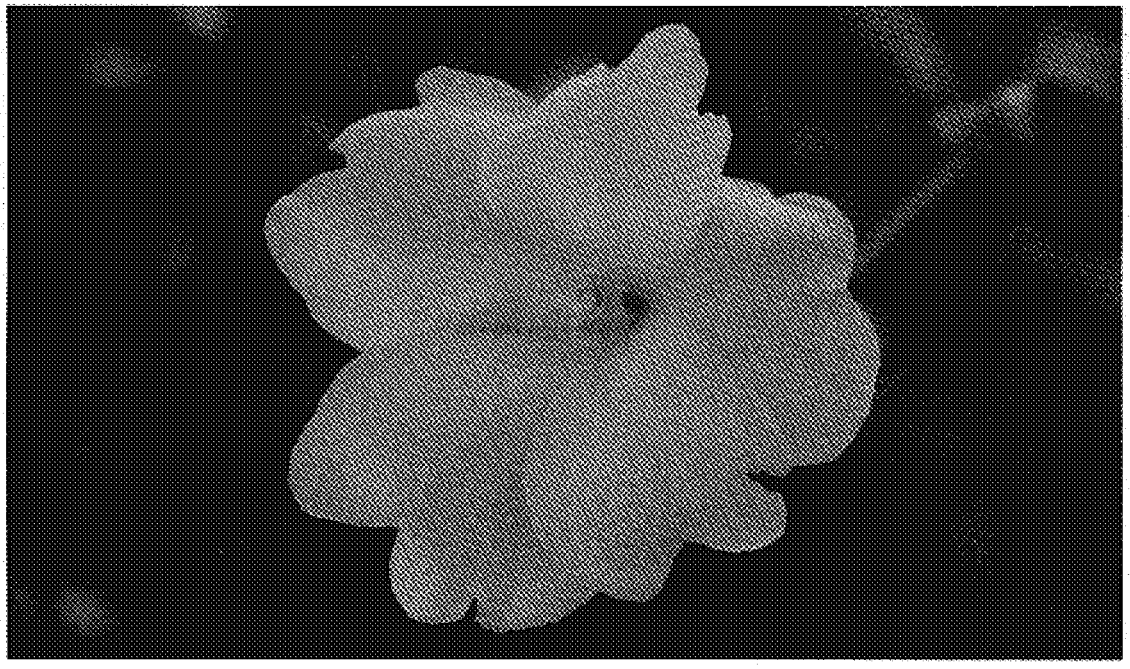
FIG. 2 shows a close-up of the mature inflorescence.

The following detailed descriptions set forth the distinctive characteristics of 'SAKIMP010'. The data which define these characteristics were collected from asexual reproductions carried out in Salinas, Calif. The plant history was taken on plants grown for about four months from propagation by terminal cuttings under greenhouse conditions. Color references are primarily to the RHS Colour Chart of The Royal Horticultural Society of London (R.H.S.), 4th edition (2001). Anatomic labels are from The Cambridge Illustrated Glossary of Botanical Terms, by M. Hickey and C. King, Cambridge University Press.

DETAILED BOTANICAL DESCRIPTION

Classification:
- *Family.*—Balsaminaceae.
- *Botanical.—Impatiens interspecific* cross, *Impatiens× hybrida* (hort).
- *Common name.—Impatiens.*

Parentage:
- *Female parent.*—'NG-01WD', an unpatented proprietary *Impatiens* breeding line with white flowers.
- *Male parent.*—'EL-1A-2', an unpatented proprietary Impatiens breeding line with lilac flowers.

Growth:

*Time to produce a rooted cutting.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

*Environmental conditions for plant growth.*—Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2–3 days, 2 times in consecutive applications and then given one clear water application. Pots were top-dressed with a dry, slow release fertilizer containing 14% nitrogen, 14% phosphorus and 14% potassium. The typical average air temperature was 24° C.

*Time to bloom from propagation.*—6 to 8 weeks.

Plant description:

*Habit.*—Vigorous and branching growth habit.

*Life cycle.*—Tender perennial.

*Height.*—30.0 cm to 32.0 cm from soil line to top of foliage.

*Spread.*—52.0 cm to 54.0 cm.

*Time to produce a rooted cutting.*—About 4 weeks.

*Flowering requirements.*—Will flower so long as temperature is above 5° C.

*Temperature tolerance.*—Plants have been observed to continuously flower at a temperature range of 5° C.–36° C., with ability to withstand high heat and humidity.

Branches:

*Number.*—14 total with 4 main branches.

*Length.*—2.0 cm from soil line to first node; 28.0 cm to 30.0 cm total.

*Diameter* (*main branch*).—1.0 cm.

*Color.*—RHS 185A (greyed-purple).

Stems:

*Stem description.*—Strong; circular cross-section, smooth and shiny.

*Length.*—5.0 cm from first to second node, 8.0 cm to 10.0 cm total.

*Diameter.*—0.6 cm to 0.8 cm.

*Internode length.*—5.0 cm.

*Color.*—RHS 185A (greyed-purple) and RHS 143B (green).

*Pubescence.*—Absent.

*Anthocyanin color.*—RHS 185D (greyed-purple).

Leaves:

*Arrangement.*—Whorled with up to 5 leaves per node; opposite if only two leaves at one node.

*Length.*—9.0 cm to 10.0 cm.

*Width.*—3.0 cm to 3.5 cm.

*Shape.*—Lanceolate, curled.

*Apex.*—Acuminate.

*Base.*—Attenuate.

*Margin.*—Ciliate.

*Texture.*—Dull, waxy.

*Color.*— *Upper surface: RHS* 139A (green). Lower surface: RHS 137C (green).

*Variegation.*—Absent.

*Fragrance.*—Absent.

*Pubescence.*—Absent.

*Venation.*—Pinnate.

*Venation color.*—Upper surface: RHS 138B (green). Lower surface: RHS 138C (green).

*Petioles.*—Length: 0.6 cm to 0.8 cm. Diameter: 0.3 cm to 0.4 cm. Color RHS 138D (green) with RHS 185D (greyed-purple). Texture: Smooth, glabrous.

Flower buds:

*Shape.*—Deltoid, longitudinal cross-section.

*Length.*—1.0 cm.

*Diameter.*—1.0 cm.

*Color.*—RHS N155B (white) on the inside with RHS 142A (green) and specks of RHS 185C (greyed-purple) on the outside.

*Texture.*—Glabrous.

Inflorescence:

*Inflorescence.*—Single flower with spur.

*Number of flowers per node.*—1 in bloom at one time; about 10 flower buds per node.

*Number of flowers per plant.*—26 at one time.

*Lastingness of individual blooms on the plant.*—14 days.

*Fragrance.*—Absent.

Peduncles:

*Length.*—5.0 cm.

*Diameter.*—0.2 cm.

Color.—RHS 138B (green).

*Texture.*—Smooth, glabrous.

Corolla:

*Shape.*—Roughly circular with 5 radial petals.

*Diameter.*—About 6.0 cm.

*Depth.*—0.1 cm to 0.2 cm.

Petals:

*Length.*—3.0 cm.

*Width.*—3.0 cm.

*Shape.*—Obcordate.

*Apex.*—Emarginate (cleaved).

*Base.*—Attenuate.

*Margin.*—Entire.

*Texture.*—Glabrous.

*Color.*—Upper surface: RHS N155B (white). Lower surface: RHS N155B (white). Eye zone: RHS N155B (white).

Spur:

*Shape.*—Tubular and curved downward.

*Color.*—RHS N155B (white).

*Length.*—5.0 cm to 6.0 cm.

*Diameter.*—0.1 cm to 0.2 cm.

Sepals.—

*Shape.*—Lanceolate.

*Number.*—Two.

*Color.*—RHS N144D (yellow-green).

*Length.*—1.0 cm.

*Diameter.*—0.8 cm.

*Apex.*—Caudate.

*Base.*—Subcordate.

*Margin.*—Entire.

*Texture.*—Glabrous.

Reproductive organs:

*Stamens.*—Form: Fused; split into 4 lobes. Number: Many. Filament length: 0.3 cm. Filament color: RHS N155B (white). Anther length: 0.4 cm. Anther color RHS N155B (white). Pollen amount: Abundant. Pollen color: RHS N155A (white). Pollen description: Powdery.

*Pistil.*—Number: 5. Stigma color: RHS 144A (green). Style color: RHS 144A (green).

*Ovary arrangement.*—Parietal.

*Ovary surface color.*—RHS N144B (yellow-green).

Fruit and seed set: No seed set observed.

Disease and insect resistance: No particular resistance or susceptibility has been observed.

COMPARISON WITH PARENTAL AND KNOWN CULTIVARS

'SAKIMP010' differs from the female parent, 'NG-01WD', an unpatented proprietary *Impatiens* plant, in that 'SAKIMP010' has white flowers with a very light pink tint and a vigorous and branching growth habit, while 'NG-01WD' has white flowers and a branching growth habit.

'SAKIMP010' differs from the male parent, 'EL-1A-2', an unpatented proprietary *Impatiens* plant in that 'SAKIMP010' has white flowers with a very light pink tint and a vigorous and branching growth habit, while 'EL-1A-2' has lilac flowers and a branching growth habit.

'SAKIMP010' is similar to the commercial Impatiens variety 'Misato FG4' (U.S. Plant Pat. No. 17,613) however, there are differences as listed in the table below:

TABLE 1

Comparison of Characteristics between 'SAKIMP010' and 'Misato FG4'

| Characteristic | 'SAKIMP010' | 'Misato FG4' |
|---|---|---|
| Growth habit | Vigorous, branching | Upright, branching |
| Petal color, upper surface | RHS N155B (White) | RHS N155A (white) |
| Petal color, lower surface | RHS N155B (White) | RHS N155A (white) with RHS 58B (red-purple) markings around the mid-vein |
| Plant Height at 4 months from transplant | 30.0 cm to 32.0 cm from soil line to top of foliage | 20.0 cm to 24.0 cm from soil line to top of foliage |
| Plant Spread at 4 months from transplant | 52.0 cm to 54.0 cm | 33.0 cm to 45.0 cm |

I claim:

1. A new and distinct cultivar of New Guinea *Impatiens* plant as shown and described herein.

* * * * *